United States Patent
Wang et al.

[11] Patent Number: 5,401,632
[45] Date of Patent: Mar. 28, 1995

[54] TRIPLE HELIX PURIFICATION AND SEQUENCING

[75] Inventors: Renfeng Wang, Dublin, Calif.; Lloyd M. Smith; Xinchun E. Tong, both of Madison, Wis.

[73] Assignee: Wisconsin Alumni Research Foundation, Madison, Wis.

[21] Appl. No.: 915,245

[22] Filed: Jul. 16, 1992

[51] Int. Cl.$^6$ ............ C12Q 1/70; C07H 21/04; C12P 19/34
[52] U.S. Cl. .................. 435/6; 435/91.5; 536/23.1; 536/24.3; 536/24.33; 935/6; 935/17; 935/78
[58] Field of Search ........... 435/6, 91.5; 536/23.1, 536/23.2, 24.3, 24.33

[56] References Cited

U.S. PATENT DOCUMENTS

| | | | |
|---|---|---|---|
| 4,795,699 | 1/1989 | Tabor et al. | 435/6 |
| 5,176,996 | 1/1993 | Hogan et al. | 435/6 |

FOREIGN PATENT DOCUMENTS

| | | |
|---|---|---|
| 0456304 | 11/1991 | European Pat. Off. |
| WO9111533 | 8/1991 | WIPO |

OTHER PUBLICATIONS

I. Radharkrishnan, et al., Am. Chem. Soc., 9022–9030 (1991), "NMR Structural Studies of Intramolecular $(Y+)_n(R+)_n(Y-)_n$ DNA Triplexes in Solution: Imino and Amino Proton and Nitrogen Markers of G·TA Base Triple Formation".

G. Fry, et al., V. 13, No. 1 (1992) Research Report, "A New Approach to Template Purification for Sequencing Applications Using Paramagnetic Particles".

T. Ito, et al., Proc. Natl. Acad. Sci., USA, vol. 89, pp. 495–498 (1992) "Sequence-Specific DNA Purification by Triplex Affinity Capture".

L. Xodo, et al., Nucleic Acids Research, Vol. 18, No. 12, 3557–3564 "Spectroscopic and calorimetric investigation on the DNA triplex formed by d(CTCTTCTTTCTTTTCTTTCTTCTC) and d(GAGAAGAAAGA) at acidic pH" (1990).

E. Kool, J. Am. Chem. Soc., 113, 6265–6266 (1991) "Molecular Recognition by Circular Oligonucleotides: Increasing the Selectivity of DNA Binding".

F. Chen, Am. Chem. Soc., 4472–4479 Biochemistry (1991) "Intramolecular Triplex Formation of the Purine–Purine–Pyrimidine Type".

E. Hornes et al., 7 Genetic Analysis 145–150 (1990) "Magnetic DNA Hybridization Properties of Oligonucleotide Probes Attached to Superparamagnetic Beads and Their Use in the Isolation of Poly(A) mRNA From Eukaryotic Cells".

G. Prakash et al., J. Chem. Soc. Chem. Comm. 1161–63 (1991) "Molecular Recognition by Circular Oligonucleotides, Strong Binding of Single-stranded DNA and RNA".

Sequenase Version 2.0 Protocol (U.S. Biochemical 1990).

Roberts et al. Proceedings National Academy of Sciences, USA (Nov. 1991) 88: 9397–9401.

Primary Examiner—Margaret Parr
Assistant Examiner—Carla Myers
Attorney, Agent, or Firm—Quarles & Brady

[57] ABSTRACT

Disclosed herein are methods, kits, and equipment for purifying single stranded circular DNA and then using the DNA for DNA sequencing purposes. Templates are provided with an insert having a hybridization region. An elongated oligonucleotide has two regions that are complementary to the insert and the oligo is bound to a magnetic anchor. The oligo hybridizes to the insert on two sides to form a stable triple helix complex. The anchor can then be used to drag the template out of solution using a magnet. The system can purify sequencing templates, and if desired the triple helix complex can be opened up to a double helix so that the oligonucleotide will act as a primer for further DNA synthesis.

10 Claims, 3 Drawing Sheets

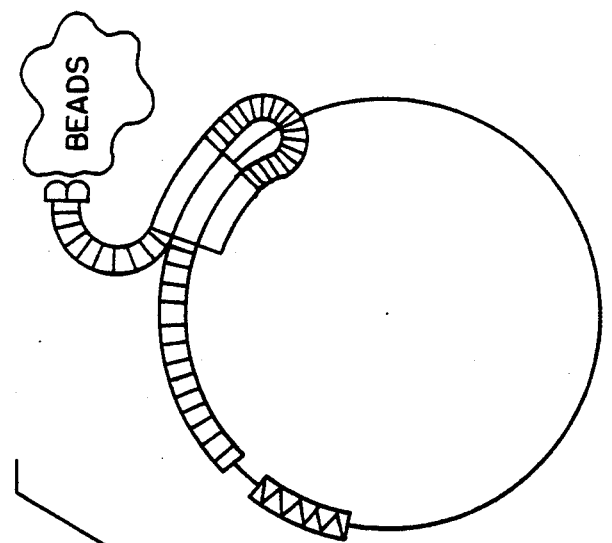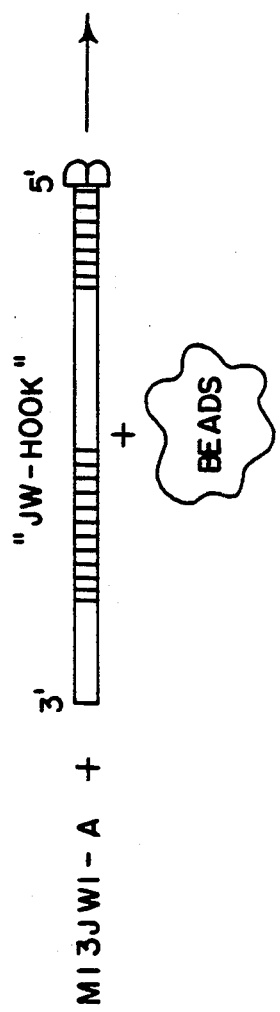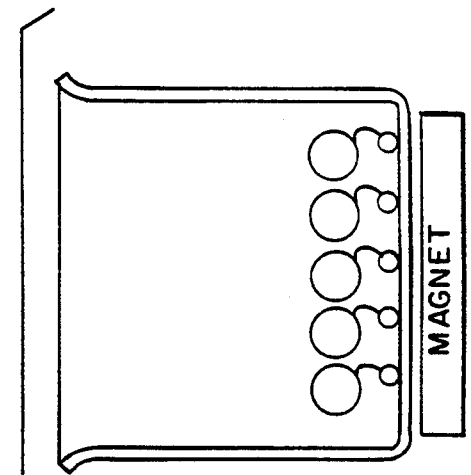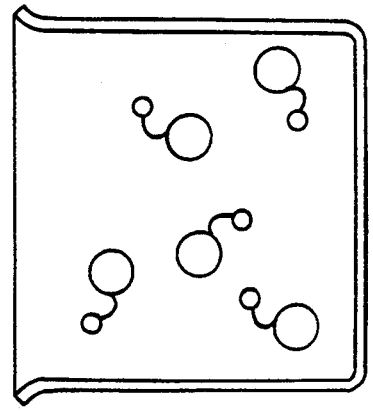
FIG. 2
FIG. 3

TRIPLE HELIX PURIFICATION AND SEQUENCING

This invention was made with United States Government support awarded by the Department of Energy (DOE), Grant No. DE FG02-90-ER61026. The United States Government has certain rights in this invention.

FIELD OF THE INVENTION

The invention relates to recombinant DNA technology. It provides an efficient way to purify circular, single stranded DNA (e.g. DNA sequencing templates), and also permits one to use an oligonucleotide that assists in the purification as a primer for a DNA sequencing reaction.

BACKGROUND OF THE INVENTION

The substantial costs and time involved in DNA sequencing are of concern, particularly in view of the "Human Genome Project", a research project that has the ultimate goal of sequencing the entire human genome. The currently preferred method of DNA sequencing is the "Sanger" (a.k.a. "dideoxy") sequencing method. See e.g. U.S. Pat. No. 4,795,699. See also "Sequenase Version 2, Step-By-Step Protocols for DNA Sequencing With Sequenase Version 2.0" by U.S. Biochemical (5th edition 1990). The disclosure of all patents and articles described herein are incorporated by reference as fully set forth herein.

In the dideoxy method, one inserts the DNA fragment to be sequenced into a circular phage template, then purifies the modified template, anneals a primer to the template, and generates therefrom four populations of single stranded DNA fragments that have one defined end, one variable end, and a radioactive portion. The variable end is a specific nucleotide (G, C, T, or A) in each grouping. The fragments are separated on the basis of their length on a high resolution gel. Each band corresponds to a specific nucleotide in the sequence, and this information is used to identify the position of the nucleotide in the sequence.

Some of the steps of this sequencing procedure have already been automated (e.g. DNA synthesis and gel analysis). However, purification of single stranded circular DNA has resisted efficient automation. One company has recently attempted to partially automate this step by developing a hybridization capture method. See G. Fry et al. 124 BioTechniques 124–131 (1992). Their method hybridizes a single stranded oligonucleotide to a complementary strand of a single stranded circular template. The oligonucleotide has an attached biotin group that is capable of binding to streptavidin-coated paramagnetic styrene beads. One end of the oligonucleotide hybridizes to the template and the other end binds (via the biotin group) to a magnetic anchor. A magnetic field is used to drag the beads (and thus the template) out of solution.

Unfortunately, this system suffers from the relatively weak hybridization of the oligonucleotide to the template. Using much longer oligonucleotides might lead to better hybridization, but would also cause other problems (e.g. cost of oligonucleotides).

In other unrelated work, there have been reports of some circular DNA that can surround a short DNA sequence on two sides to form a triple helix (E. Kool, 113 J. Am. Chem. Soc. 6265–6266 (1991)), and other reports that certain single stranded oligonucleotides can hairpin around both sides of a short non-circular single stranded oligonucleotide to form a triple helix (L. Xodo et al., 18 Nuc. Acids Res. 3557–3564 (1990)).

SUMMARY OF THE INVENTION

In one aspect, the invention provides a triple helix complex. It is formed from a recombinant circular single stranded DNA which has a purine rich tract of at least five nucleotides, and a single stranded oligonucleotide having two pyrimidine rich tracts, each being at least five nucleotides. The pyrimidine rich tracts are spaced apart so as to be able to sandwich the purine tract and hybridize thereto. The oligonucleotide is bound to a chemical anchor that is capable of being bound to a support. In a preferred form, the support contains paramagnetic particles that are capable of being attracted by a magnetic field. For example, the oligonucleotide can be biotinylated, the biotin can be bound to a polystyrene bead coated with avidin, and the avidin can be coated on a paramagnetic bead.

In another aspect, the invention provides a kit for purifying circular DNA from solution. The kit has recombinant double stranded circular DNA having a purine rich tract of at least five nucleotides on at least one strand, and a restriction enzyme site suitable for insertion of the DNA to be sequenced. A single stranded oligonucleotide is also provided that has two pyrimidine rich tracts, each being at least five nucleotides. If desired, the oligonucleotide can be biotinylated, and the kit can also contain beads coated with avidin and containing a paramagnetic substance that can be moved by a magnetic field.

In another aspect, the invention provides a method of separating a single stranded circular DNA from a solution. The DNA has a hybridization tract of at least five nucleotides. The method involves hybridizing to two sides of the tract a DNA single stranded oligonucleotide so as to form a triple helix complex. Thereafter, one exposes the solution to a magnetic field so that an anchor bound to the oligonucleotide will cause the circular DNA to be separated from the solution. Preferably, the hybridization step occurs in mildly acidic conditions (pH 4–6), and there is a further step of using the oligonucleotide as a primer for forming a DNA strand along (and complementary to) a part of the single stranded circular DNA. The DNA synthesized in this manner can also be purified using the magnetic field.

In yet another aspect, the invention provides an apparatus for automating the above method. It has a container, a device to project a magnetic field into the container, an automatic pipette system for delivering and removing fluids from the container, and the above oligonucleotide.

The oligonucleotide acts as a "biological lasso" and binds with great stability to the template. It is interesting that this occurs because, inter alia, the oligonucleotide must bind to both the outside and the inside of circular DNA. Moreover, by using neutral or mildly basic conditions, the triple helix complex will change to a double helix that serves as a pre-primed template.

An object of the present invention therefore includes providing methods of the above kind that permit purification of single stranded circular DNA by automated means.

Another object is to provide complexes and kits for use in such methods.

Another object is provide oligonucleotides for use in such methods in which the oligonucleotides both assist in the purification and act as a primer for DNA synthesis.

Yet another object of the invention is to provide equipment to automate such methods.

These and still other objects and advantages of the present invention will be apparent from the description which follows. The following detailed description merely recites examples of the present invention. It is not intended to represent the full scope of the invention. Rather, the claims should be looked to in order to determine the full scope.

THE DRAWINGS

FIG. 2 is a schematic of how the template can be purified in accordance with the present invention;

FIG. 3 is a schematic of how a magnetic field can be used as part of the purification process.

DESCRIPTION OF THE PREFERRED EMBODIMENTS

M13mp18, RF DNA (double stranded) was purchased from New England Biolabs. It is a recombinant phage having a polycloning restriction site. The present invention uses one of the sites (Hind III) to insert a hybridization tract, and preferably another of these sites (e.g. EcoRI) to insert the DNA to be sequenced.

Three single stranded oligonucleotides were synthesized on a standard DNA synthesizer. The hybridization tract was formed from two of these nucleotides: 5-AGCT-TAAAAAGAAAAGAAAAAAAGAAAAAAGA-AAGAA-3' (SEQ ID NO:1) which is the preferred purine rich tract; and its complementary strand (with Hind III compatible 4-base overhangs) overhangs), 5' AGCTTTCTTTCTTTTTTTCTTTTTTTCTTTTCT-TTTTA-3' (SEQ ID NO:2). The preferred hairpin oligonucleotide is:

5'-CACACTTTTTCTTTTCTTTTTTT-CACACTTTTTTTTCTTTTCTTTTT-3' (SEQ ID NO:3).

Figure 1:
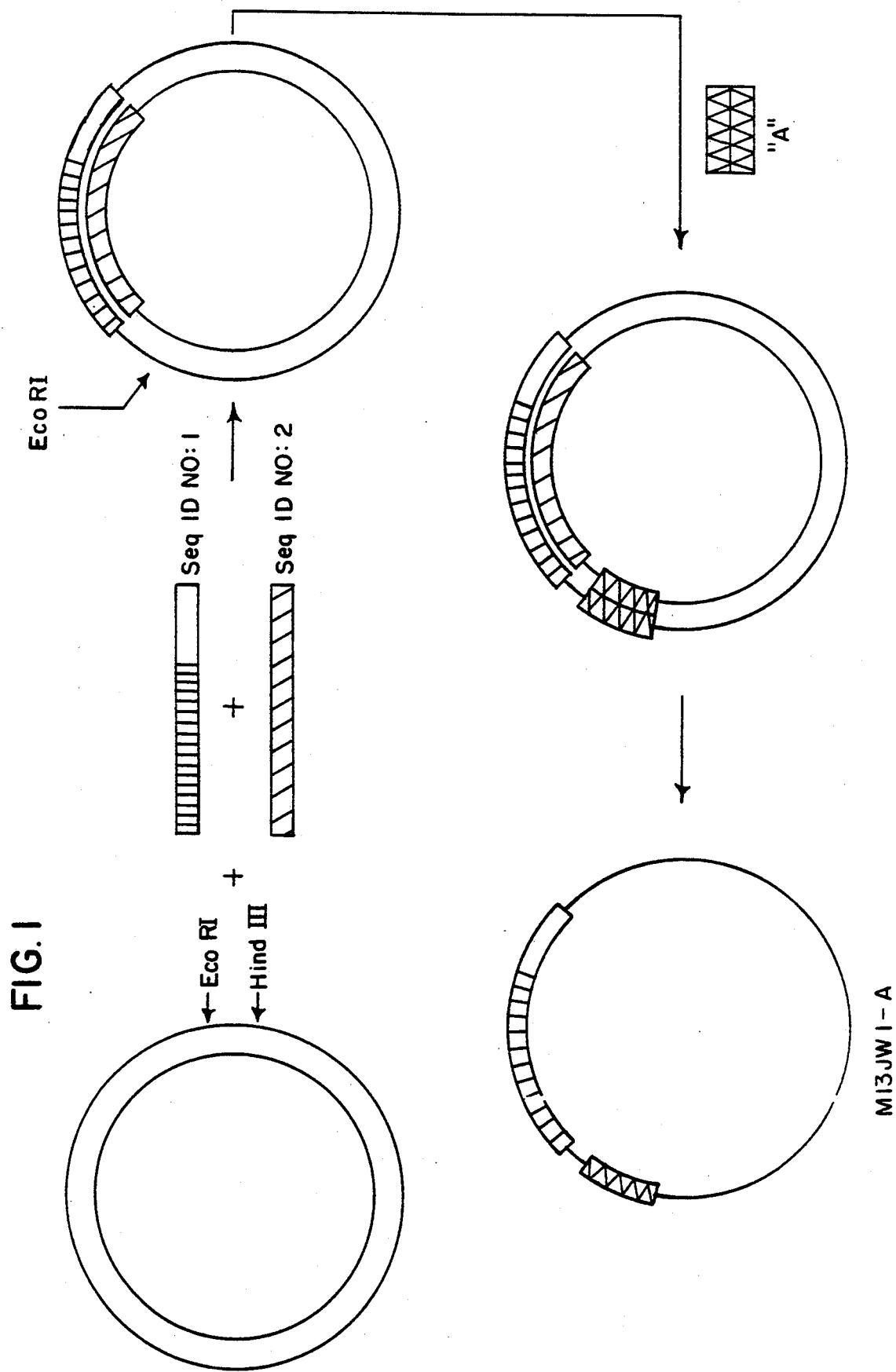
FIG. 1 is a schematic of a preferred method of inserting DNA to be sequenced into a vector along with a hybridization tract.

Restriction enzyme Hind III (New England Biolabs) was used to cut the M13mp18 RF DNA in the buffer provided by the vendor, using standard conditions. The restriction digestion solution was incubated at 37° C. for thirty minutes. The enzyme was then deactivated by heating the solution at 90° C. for five minutes. SEQ ID NO:1 and SEQ ID NO:2 were added to the above solution. The solution was then heated to 85° C. and then slowly cooled to room temperature. T4 DNA ligase (New England Biolabs) was then added using standard conditions along with the ligation buffer provided with the enzyme. The solution was then kept at 12° C. for sixteen hours. See FIG. 1.

DNA in ligation solution is then transformed into *E. Coli* using standard techniques. In our particular case we used a Transffinity kit made by BRL. A plaque was picked up and grown in culture medium at 37° C. Cells can be obtained and lysed using standard conditions to obtain the double stranded phage.

A selected DNA segment to be sequenced (e.g. "A") can be inserted at the EcoRI site using standard EcoRI restriction enzyme conditions, followed by ligation. The "double insertion" vector can then be transformed using similar techniques in *E. Coli* except that this time the supernatant will be of interest. It will be phage solution containing the single stranded circular vector M13JW1-A. After centrifugation, the phage solution can be stored at 4° C. for further experiments.

Prior to use, SEQ ID NO:3 was biotinylated on an Applied Biosystems automated synthesizer using biotin phosphoramidite. See e.g. G. Fry et al., 13 BioTechniques 124, 126 (1992) (automated biotinylation). The biotinylated SEQ ID NO:3 was named "JW-Hook". It is pyrimidine rich in two regions and homologous in those two regions to two purine rich regions of SEQ ID NO:1. As used herein, a region is "rich" if over seventy percent of the region is of the specified type.

Examples of pyrimidine bases are thymine (T), cytosine ("C"), and uracil (U). Examples of purine base are adenine ("A") and guanine ("G"). There are also other known purine and pyrimidine bases. See A. Lehninger, Biochemistry, 242 (1970).

Purification

As depicted in FIG. 2, one half pmole of JW-Hook can be added to 100 microliters of M13JW1-A phage solution at pH 5 (0.2M sodium acetate buffer) in the presence of $MgCl_2$). The solution will also contain 0.01% SDS to break up the phage proteins. The total volume of the solution is 200 microliters. After incubation at 50° C. for fifteen minutes, Dynalbeads M-280 streptavidin are added, and the solution is incubated at 37° C. for another fifteen minutes. Dynal beads M-280 streptavidin are superparamagnetic polystyrene beads with streptavidin covalently attached to the bead surface.

A magnetic field can be applied to the solution to separate the beads from the rest of the solution. When the beads are dragged out of the solution in response to the magnetic field, the biotin will also be dragged out. As the biotin is in turn bound to the oligonucleotide, and as the oligonucleotide has hybridized the template, the template is automatically dragged out of solution with the beads.

The DNA can then be eluted from the beads by adding 20 microliters of 0.01 molar pH 9 tris-HCL buffer and heating to 65° C. for five minutes. The change in pH causes the triple helix complex structure to open up into a double stranded complex, and the heating will split the oligonucleotide from the template. The magnetic field can continue to hold the oligonucleotide while the template can then dissolve into a solution. In one experiment, a recovery of nearly 100% of M13JW1 (without the "A" insert) was achieved through this technique.

Sequencing

Figure 4:
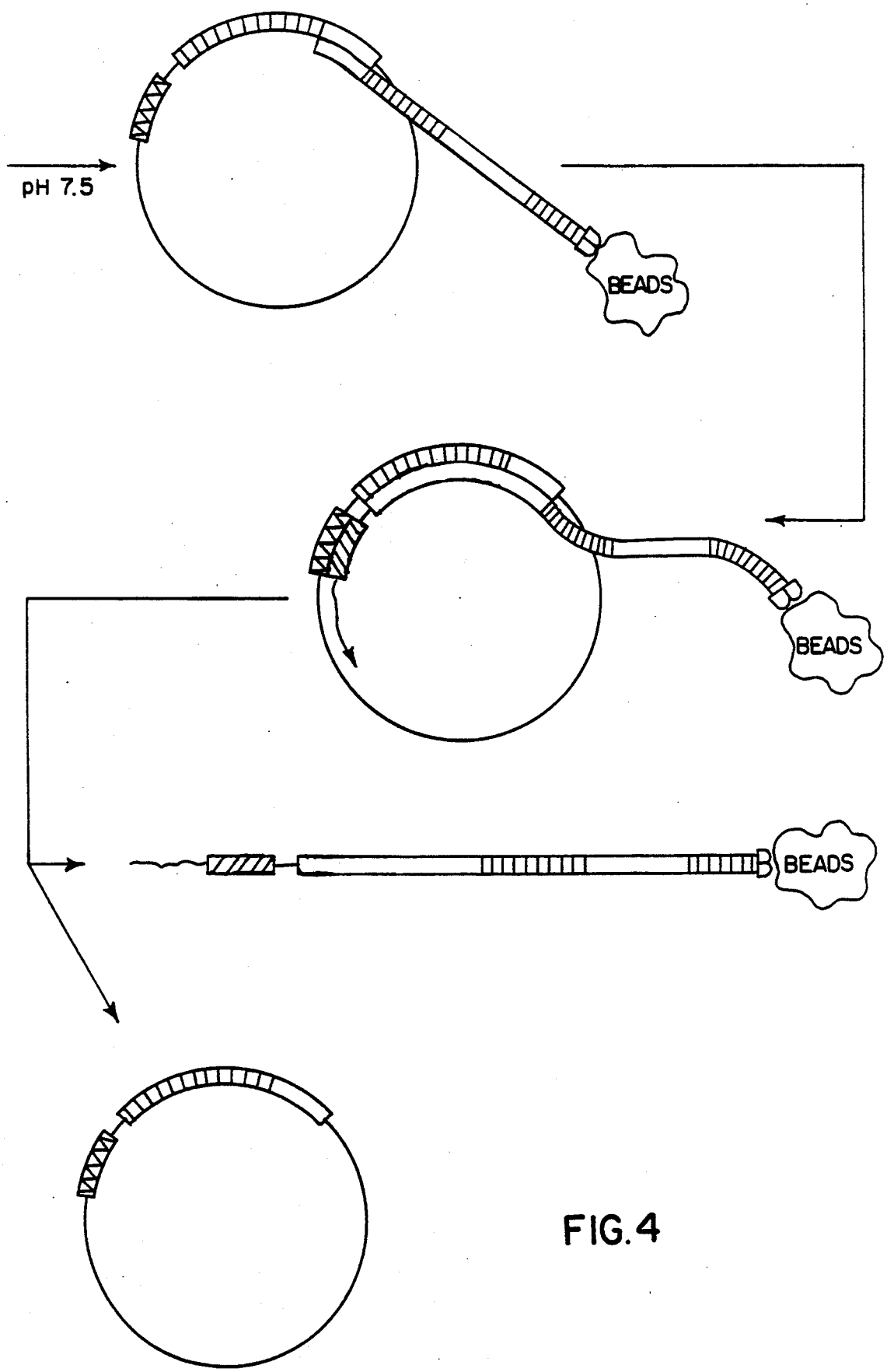
FIG. 4 is a schematic of how the product of FIG. 2 can be used for DNA synthesis as part of a sequencing reaction.

One can use a conventional primer with the purified template and follow sequencing/synthesis procedures such as those of U.S. Pat. No. 4,795,699 and/or the U.S. Biochemical "Sequenase" kit. Both use T7 DNA Polymerase to cause a DNA synthesis using dideoxy sequencing reaction reagents. In the alternative, the complex can be left intact (albeit resuspended by turning off the magnetic field and adding seven microliters of water). DNA sequencing using the Sequenease kit can then be performed by replacing the Sequenease template with the complex (and by not adding their primer). In this regard, at typical pH levels of DNA synthesis (e.g. pH 7.5) the triple helix complex opens up sufficiently such that the 3' end of the oligonucleotide acts as a sequencing primer (see FIG. 4).

Note that if insert "A" has been added, it will be sequenced along with the portion of the M13mp18 near the cloning site. If not, only the template will be sequenced.

Yet another possibility is that after purification of single stranded M13JW1-A another lasso (similar to JW-Hook but with other attributes desirable for sequencing) could serve as a primer. The following illustrates this possibility.

EXAMPLE

Bst DNA polymerase was obtained from Bio-Rad (Richmond, Calif.). Single stranded M13mp19 template DNA was prepared by standard methods. A modified M13 sequencing primer (denoted B-BT) with the sequence 5'-CAT* GAC GTT GTA AAA CGA CGG CCA GT-3' (SEQ ID NO:4) was synthesized by the University of Wisconsin on an Applied Biosystems 381A DNA synthesizer. Instead of being biotinylated at the end of the oligo, the third nucleotide on the oligo was modified to permit anchoring.

T* is the product obtained from use of the modified nucleoside phosphoramidite amino-modifier-dT (Glen Research, Sterling, Va.), which has a primary amino group attached to thymine with a 10-atom spacer arm. This amino group was coupled to NHS-LC-Biotin (Pierce, Rockford, Ill.) as described in Dynabeds M-280 Technical Handbook; Magnetic DNA Technology 6. A biotinylated primer was purified by reverse-phase high-performance liquid chromatography and 5' end-labeled using polynucleotide kinase (USB, Cleveland, Ohio) and [$\gamma^{32}P$] at 5000Ci/mmol (Amersham, Arlington Heights, Ill.).

Streptavidin-coupled magnetic beads (Dynabeads M-280, Dynal, Inc., Great Neck, N.Y.) were utilized as a solid support. A ½"×½" neodymium-iron-boron magnet (Bunting Magnetics, Newton, Kans.) was used to immobilize the beads during the supernatant removal and washing steps. The beads were pre-washed in 1× TES (10 mM Tris-HCl, 1 mM EDTA, 1M NaCl, pH 8.2) three times and resuspended at 10 µg/µl in 1× TES.

DNA sequencing reactions were performed by mixing 0.8 pmol of template DNA, 0.8 pmol of 5'-$^{32}P$ end labeled primer, and 1.5 µl of 10× SB (SB, or sequence buffer, was 10 mM MgCl$_2$ and 10 mM Tris-HCl pH 8.5). Water was added to give a total volume of 10 µl. This mixture was placed at 65° C. (heating block) for 2 minutes, at 37° C. (heating block) for 5 minutes, and at room temperature (air) for 10 minutes to anneal the primer to the template. 0.5 µl of Bst DNA polymerase (1 unit/µl, Bio-Rad, Richmond, Calif.) added, and 2.5 µl of the resultant enzyme/DNA mixture was placed in each of four tubes containing 2.0 µl of d/ddNTP mixture. The sequencing reactions were placed at 65° C. for five minutes, followed by the addition of 2.0 µl of a solution containing 10 mM EDTA (diluted from a 0.5M solution of disodium EDTA which had been adjusted to pH 8.2 with NaOH)and 95% formamide to stop the reaction. They were denatured by heating at 90° C. for 5 minutes, and immediately placed on ice before either loading on an acrylamide gel for analysis or binding to magnetic particles for purification.

The newly synthesized DNA fragments were bound to streptavidin-coated magnetic beads by adding 2.0 µl of the bead suspension and 2.0 µl of 5× BB (BB, or binding buffer, is 1× TES and 0.2% Tween-20) to each reaction tube. The tube was placed at room temperature for 15 minutes to allow binding to take place. The supernatant was removed and the beads washed using the magnet to immobilize the beads in the tubes. The beads were washed twice with 10 µl 1× TES buffer, and once with 10 µl H$_2$O. The DNA fragments were eluted from the beads in 6.5 µl stop solution (10 mM EDTA, 95% formamide, 0.05% bromophenol blue) at 90° C. for 5 minutes. Approximately 1.5 µl of supernatant were loaded on a 6% denaturing polyacrylamide gel for sequence analysis.

It will be appreciated that in this procedure sequencing reactions are performed in solution by standard procedures, except that a biotinylated primer is employed. In this example the primer was a 26 mer biotinylated at an amino-modified T nucleoside three bases from the 5' end. The primer sequence was chosen to be complementary to the M13 sequence at all positions other than the modified T, which replaced a C normally at that position. The choice of an internal position for the biotin group left the 5' terminus of the primer free for labeling with $^{32}P$ using polynucleotide kinase.

The sequencing reactions are denatured to separate the newly synthesized fragments from the template strand, and the fragments are captured on streptavidin-conjugated magnetic beads in a fifteen minute incubation at room temperature. The inclusion of the detergent Tween-20 in the binding buffer was found to be desirable for minimizing non-specific binding. Contaminating species are removed by washing the beads after immobilizing them in the sample tube with a fixed magnet. The resulting pure single-stranded DNA fragments are eluted from the solid support by heating at 90° C. in 10 mM EDTA and 95% formamide, and may be loaded directly onto a denaturing polyacrylamide gel for sequence analysis.

In order to further increase the binding efficiency, the denaturation conditions were investigated. The best conditions found employed a 5 minute denaturation at 90° C. in the presence, of 29% formamide and 3.0M EDTA followed by immediate incubation on ice, and resulted in a binding efficiency of about 80%. A 10 mM EDTA, 95% formamide solution gave efficient elution for temperatures of 65° C. or greater.

Apparatus

A preferred automated apparatus for performing the above method is a 96 well microtiter plate, together with a system for causing a magnetic field, and an automated pipette system. Biotinylated oligonucleotide, plus the beads and the vector are added. The magnetic field separates out the triple helix complex, and the supernatent can be removed by the pipette system. At this point, in the same wells, the additional reagents for sequencing are added by the pipette system. The 96 wells can be divided into four groups of 24, each group receiving a different dideoxy. Upon completion of the DNA synthesis, the magnetic field can be reactivated to remove undesired reagents.

It will be appreciated that the present system provides an automatable technique for purifying sequencing templates and the like. A single stranded oligonucleotide is able to form a stable triple helix complex that acts as a lasso. By changing the pH one can open up the complex, thereby permitting the same oligonucleotide to function as an anchored primer. In the alternative a radiolabelled primer that is internally biotinylated an be used as a primer, and magnetic purification can be used during the sequencing step.

It should be appreciated that variations to the preferred embodiments can be made without departing from the scope of the invention. For example, if it is desired to perform the synthesis step without attached magnetic beads, it should be possible to break the avidin biotin bond, and then use biotinylated oligonucleotide bound to the template as a primer. At the end of the sequencing reaction, one can add back the magnetic beads (thereby rebinding biotin to the beads).

The most highly preferred form of the invention has a purine rich tract on the template and pyrimidine rich tracts on both sides of it on the oligonucleotide. However, the core idea is that the nucleotide sequences at two regions on the oligonucleotide must be substantially or entirely complementary to a single nucleotide region on the insert (with a relatively short sequence in between, preferably four to ten sequences).

The length of the tracts should preferably be at least five. The longer the sequence, the better the hybridization. However, as length begins to increase over twenty five, other problems begin to arise.

While an avidin/biotin system for linking the oligo to a support has been described, the core of the concept is to attach the oligo via a chemical anchor to a support. The support is preferably a paramagnetic bead, but could simply be an avidin bead that permits separation by centrifugation. Various other chemical anchoring/support systems may also be used.

Note also that while M-13 phages are preferred, the invention should be generally applicable to purifying circular single stranded DNA.

We claim:

1. A triple helix complex, comprising:
a single stranded oligonucleotide having two pyrimidine rich nucleotide tracts, wherein each of the pyrimidine rich nucleotide tracts have over 0.7 times eighteen pyrimidine nucleotides, wherein the two pyrimidine rich nucleotide tracts have mirror symmetry of said pyrimidine nucleotides with respect to each other; and
a recombinant, circular single stranded DNA having a purine rich nucleotide tract having over 0.7 times eighteen purine nucleotides wherein that portion of the purine rich nucleotide tract in the triple helix complex is complementary to that portion of both pyrimidine rich nucleotide tracts in the triple helix complex; and
wherein in the triple helix complex both pyrimidine rich nucleotide tracts of said single stranded oligonucleotide are hybridized to the same purine nucleotide bases of the circular DNA's purine rich nucleotide tract, and so that one of the pyrimidine tracts is oriented 5' to 3' in the complex and the other is oriented 3' to 5' in the complex, wherein the 5'to 3' and 3' to 5' orientation of the pyrimidine tracts is in reference to one another; and
wherein the three tracts in the triple helix complex are of the same size and are of sufficient size so as to permit formation of the complex from the three tracts at an acidic condition of between pH 4.0 and pH 6.0.

2. The complex of claim 1, wherein a portion of the oligonucleotide is bound to a chemical anchor.

3. The complex of claim 2, wherein the chemical anchor is bound to a support.

4. The complex of claim 3, wherein the support is capable of being attracted by a magnet.

5. The complex of claim 2, wherein the oligonucleotide is bound to biotin and the biotin is bound to a paramagnetic bead.

6. A method of separating the triple helix complex of claim 1 from a solution that contains the complex, comprising:
exposing the solution to a magnetic field such that a support bound to the oligonucleotide of claim 1 cause the triple helix complex to be separated out from the solution.

7. The method of claim 6, comprising the further step of using the oligonucleotide as a primer bound in a double helix complex to the same circular single stranded DNA to form a DNA strand along, and complementary to, a part of the single stranded circular DNA.

8. The method of claim 7, further comprising the step of purifying the formed DNA strand of claim 10 using a magnetic field.

9. A kit for forming the triple helix complex of claim 1, comprising:
the recombinant, circular single stranded DNA of claim 1;
the oligonucleotide of claim 1; and
wherein the oligonucleotide and recombinant, circular single stranded DNA are not hybridized to each other.

10. The kit of claim 9, wherein the oligonucleotide is biotinylated, and the kit further comprises avidin coated beads that can be moved by a magnetic force.

* * * * *

UNITED STATES PATENT AND TRADEMARK OFFICE
CERTIFICATE OF CORRECTION

PATENT NO. : 5,401,632
DATED : March 28, 1995
INVENTOR(S) : Renfeng Wang

It is certified that error appears in the above-indentified patent and that said Letters Patent is hereby corrected as shown below:

Column 3, line 41, delete second occurrence of "overhangs)".

Column 6, line 42, replace "presence," with --presence--.

Column 10, line 33, claim 6, change "cause" with --causes--.

Column 10, line 42, claim 8, change "[10]" to --7--.

Signed and Sealed this

Twenty-third Day of May, 1995

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:1:

AGCTTAAAAA GAAAGAAAA AAAGAAAAAA GAAAGAA 37

( 2 ) INFORMATION FOR SEQ ID NO:2:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:2:

AGCTTTCTTT CTTTTTCTT TTTTCTTTT CTTTTTA 37

( 2 ) INFORMATION FOR SEQ ID NO:3:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:3:

```
CACACTTTTT  CTTTTCTTTT  TTTCACACTT  TTTTTCTTTT  CTTTTT                                46
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:4:

```
CANGACGTTG  TAAAACGACG  GCCAGT                                                        26
```